US008603025B2

(12) United States Patent
Pongratz et al.

(10) Patent No.: US 8,603,025 B2
(45) Date of Patent: Dec. 10, 2013

(54) GAS-ASSISTED FLUID-DISPENSING DEVICE

(75) Inventors: Troy Allen Pongratz, Minneapolis, MN (US); Bradley David Robb, Maple Plain, MN (US); Jon E. Hoogenakker, Inver Grove Heights, MN (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 13/576,833

(22) PCT Filed: Mar. 24, 2011

(86) PCT No.: PCT/US2011/029763
§ 371 (c)(1),
(2), (4) Date: Aug. 2, 2012

(87) PCT Pub. No.: WO2011/119811
PCT Pub. Date: Sep. 29, 2011

(65) Prior Publication Data
US 2013/0006170 A1 Jan. 3, 2013

Related U.S. Application Data

(60) Provisional application No. 61/317,138, filed on Mar. 24, 2010.

(51) Int. Cl.
*A61M 37/00* (2006.01)
(52) U.S. Cl.
USPC ............................................. 604/24; 604/141
(58) Field of Classification Search
USPC .......... 604/24–25, 82–92, 140–147, 218–231
See application file for complete search history.

(56) References Cited

U.S. PATENT DOCUMENTS

| 6,059,749 | A | * | 5/2000 | Marx | 604/82 |
| 6,260,737 | B1 | | 7/2001 | Gruendeman | |
| 6,464,663 | B1 | * | 10/2002 | Zinger | 604/82 |
| 2004/0134494 | A1 | * | 7/2004 | Papania et al. | 128/203.12 |

OTHER PUBLICATIONS

U.S. Patent and Trademark Office, International Preliminary Report on Patentability in PCT Application Serial No. PCT/US2011/029763, Aug. 6, 2012.
U.S. Patent and Trademark Office, International Search Report and Written Opinion in PCT Application Serial No. PCT/US2011/029763, May 20, 2011.

* cited by examiner

*Primary Examiner* — Kevin C Sirmons
*Assistant Examiner* — Phillip Gray
(74) *Attorney, Agent, or Firm* — Wood, Herron & Evans, L.L.P.

(57) ABSTRACT

A gas-assisted fluid-dispensing device (10) for delivering an aerosol. The gas-assisted fluid-dispensing device (10) includes a syringe (14) that contains a fluid and includes a distal end (18), a proximal end (20), and a plunger (24) extending proximally from the proximal end (20). A spray nozzle tip (26) is configured to generate the aerosol and is coupled to the distal end (18) of the syringe (14). The gas-assisted fluid-dispensing device (10) further includes a housing (44) having first and second housing portions (52, 54). The first housing portion (52) includes a docking port (42) for receiving the syringe (14); the second housing portion (54) is configured as a handle. A trigger (50), coupled to the housing (44), is operably coupled to an actuating member (58) that is configured to apply a force onto the plunger (24) of the syringe (14) and discharge the fluid from the syringe (14) and into the spray nozzle tip (26). A self-contained pressurized gas source (72) is coupled to the housing (44) such that it moves with the housing (44) and is also coupled to the spray nozzle tip (26). Delivery of a pressurized gas to the spray nozzle tip (26) is controlled by a control mechanism (76) and atomizes the fluid to generate the aerosol.

17 Claims, 7 Drawing Sheets

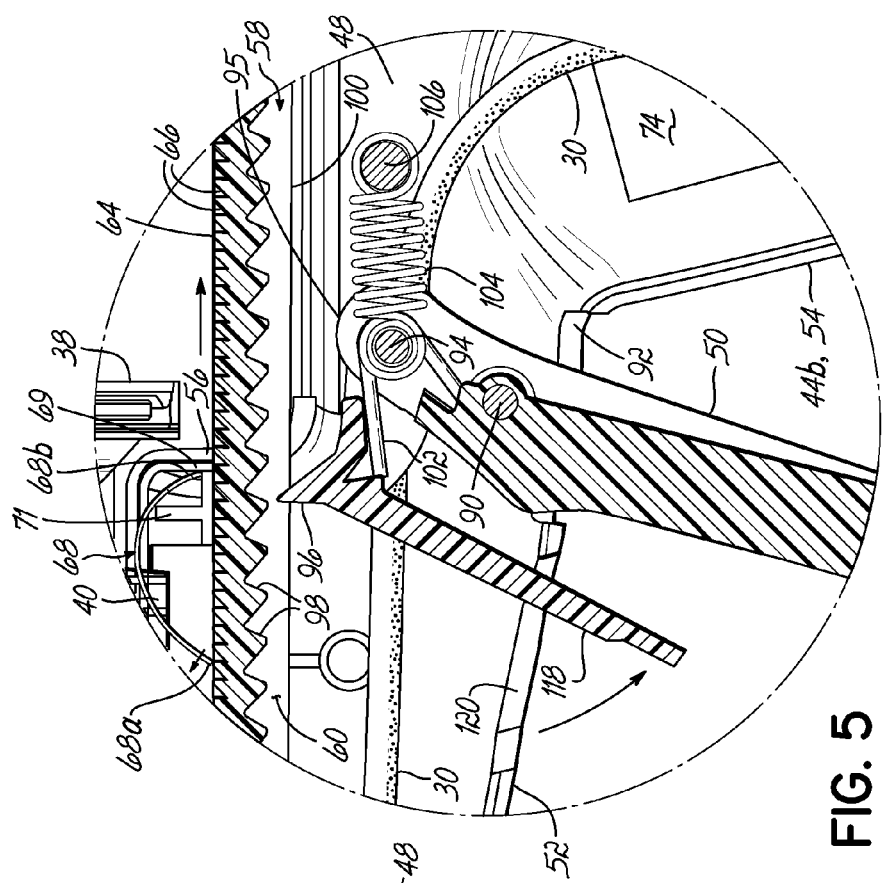
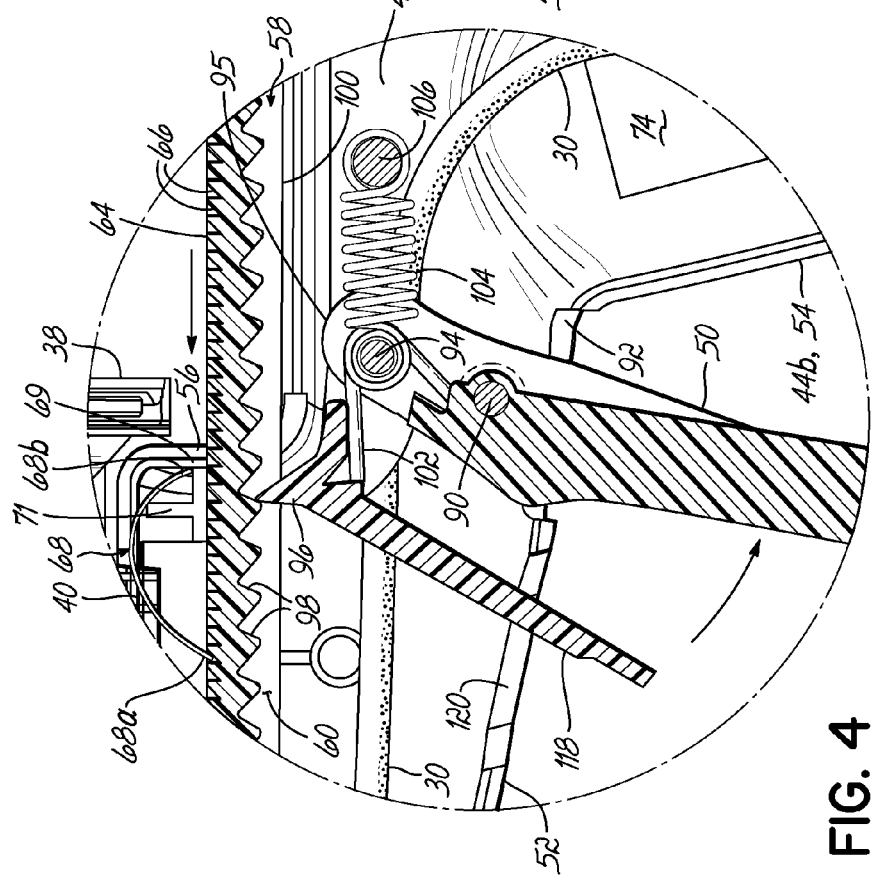

GAS-ASSISTED FLUID-DISPENSING DEVICE

CROSS-REFERENCE TO RELATED APPLICATION

This application claims the benefit of U.S. Provisional Patent Application Ser. No. 61/317,138, filed on Mar. 24, 2010, the disclosure of which is incorporated by reference herein.

TECHNICAL FIELD

This invention generally relates to fluid-dispensing devices, and particularly to a gas-assisted fluid-dispensing device configured to dispense aerosols.

BACKGROUND

In the medical field, a surgeon routinely needs to deliver a drug or another fluid to an anatomical surface within a surgical site in a patient. Conventional manual and non-manual syringes are often used to deliver these fluids to the surgical site. For example, one known conventional syringe design includes two barrels, each containing separate fluids, that are simultaneously dispensed and mixed to form a coating adapted to prevent bleeding at the surgical site. In order to spread the coating over a surface area at the surgical site, the double-barreled syringe may be coupled to a known mixing or blending spray tip, such as the FIBRIJET brand of blending tips, such as model SA-3692, that is commercially available from Micromedics of St. Paul, Minn. The blending spray tip receives the fluids from each of the two barrels, along with a pressurized gas from a pressurized gas source, to form a therapeutic aerosol that is sprayed over the surface to be coated. The therapeutic aerosol, including, for example, pain relievers, antibiotics, or coagulants, may be applied to the surgical site before, during, or after a surgical procedure.

Known conventional gas-assisted fluid-dispensing devices require a separate pressurized gas source and regulator coupled to the spray tip via tubing, and the plungers of the double-barreled syringe must be manually actuated to spray the therapeutic aerosol. However, manual actuation of the syringes may be difficult to accurately control, especially with highly viscous fluids. Furthermore, tethering of the fluid-dispensing device to the pressurized gas source and regulator may limit mobility and be somewhat cumbersome when working within a small surgical site.

There is a need, therefore, for a gas-assisted fluid-dispensing device that addresses these and other problems associated with conventional fluid-dispensing devices.

SUMMARY

According to one embodiment of the invention, an illustrative gas-assisted fluid-dispensing device is described for delivering an aerosol onto a surgical site of a patient. The gas-assisted fluid-dispensing device includes a syringe that contains a fluid. The syringe includes a distal end, a proximal end, and a plunger extending proximally from the proximal end. A spray nozzle tip, which is configured to generate the aerosol, is coupled to the distal end of the syringe. The gas-assisted fluid-dispensing device further includes a housing having first and second housing portions. The first housing portion includes a docking port for receiving the syringe; the second housing portion is configured as a handle. A trigger, which is coupled to the housing, is operably coupled to an actuating member that is configured to, when the trigger is actuated, apply a force onto the plunger of the syringe and thereby discharge the fluid from the syringe and into the spray nozzle tip. A self-contained pressurized gas source is coupled to the housing such that it moves with the housing and is also coupled to the spray nozzle tip. The delivery of a pressurized gas from the self-contained pressurized gas source is controlled by a control mechanism. Delivery of the pressurized gas to the spray nozzle tip atomizes the fluid within the spray nozzle tip and generates the aerosol.

In accordance with another illustrative embodiment of the invention, an actuator gun for use with a gas-assisted fluid-dispensing device is described. The gas-assisted fluid-dispensing device includes a syringe that contains a fluid and a spray nozzle tip coupled to the syringe. The actuator gun includes a housing having first and second housing portions. The first housing portion includes a docking port for receiving the gas-assisted fluid-dispensing device; the second housing portion is configured as a handle. A trigger, which is coupled to the housing, is operably coupled to an actuating member that is configured to, when the trigger is actuated, apply a force to the syringe and thereby discharge the fluid from the syringe and into the spray nozzle tip. A self-contained pressurized gas source is coupled to the housing such that it moves with the housing and is also coupled to the spray nozzle tip. The delivery of a pressurized gas from the self-contained pressurized gas source is controlled by a control mechanism. Delivery of the pressurized gas to the spray nozzle tip atomizes the fluid within the spray nozzle tip and generates the aerosol.

A method of dispensing an aerosol onto a surgical site according to another illustrative embodiment of the invention is described. The aerosol is dispensed by a fluid-dispensing device having a syringe of fluid and a spray nozzle tip coupled to the syringe. The fluid-dispensing device further includes a housing having first and second housing portions, wherein the first housing portion includes a docking port for receiving the gas-assisted fluid-dispensing device and the second housing portion is configured as a handle. A trigger, as well as a self-contained pressurized gas source, are coupled to the housing. The method includes supplying a pressurized gas to the spray nozzle tip by actuating the pressurized gas source. The trigger is engaged, which delivers fluid from the syringe into the spray nozzle tip. The fluid within the spray nozzle tip is atomized by the delivered pressurized gas to form the aerosol, which is dispensed from the spray nozzle tip onto the surgical site.

BRIEF DESCRIPTION OF THE DRAWINGS

FIG. 1 is a perspective view of one embodiment of a gas-assisted fluid-dispensing device.

FIG. 2 is an exploded view of the gas-assisted fluid-dispensing device of FIG. 1.

FIG. 3 is a side-elevational view of the gas-assisted fluid-dispensing device of FIG. 1 with a left side of the housing removed and showing the trigger and the actuating slide in a first position before depression of the trigger.

FIG. 4 is a cross-sectional view of the encircled area 4 of the gas-assisted fluid-dispensing device of FIG. 1 showing the trigger and the actuating slide in a second position after depression of the trigger.

FIG. 5 is a cross-sectional view, similar to FIG. 4, of the gas-assisted fluid-dispensing device of FIG. 1 showing the pawl disengaged from the actuating slide.

FIG. 6 is a perspective view of another embodiment of a gas-assisted fluid-dispensing device.

FIG. 7 is an exploded view of the gas-assisted fluid-dispensing device of FIG. 6.

Figure 6:
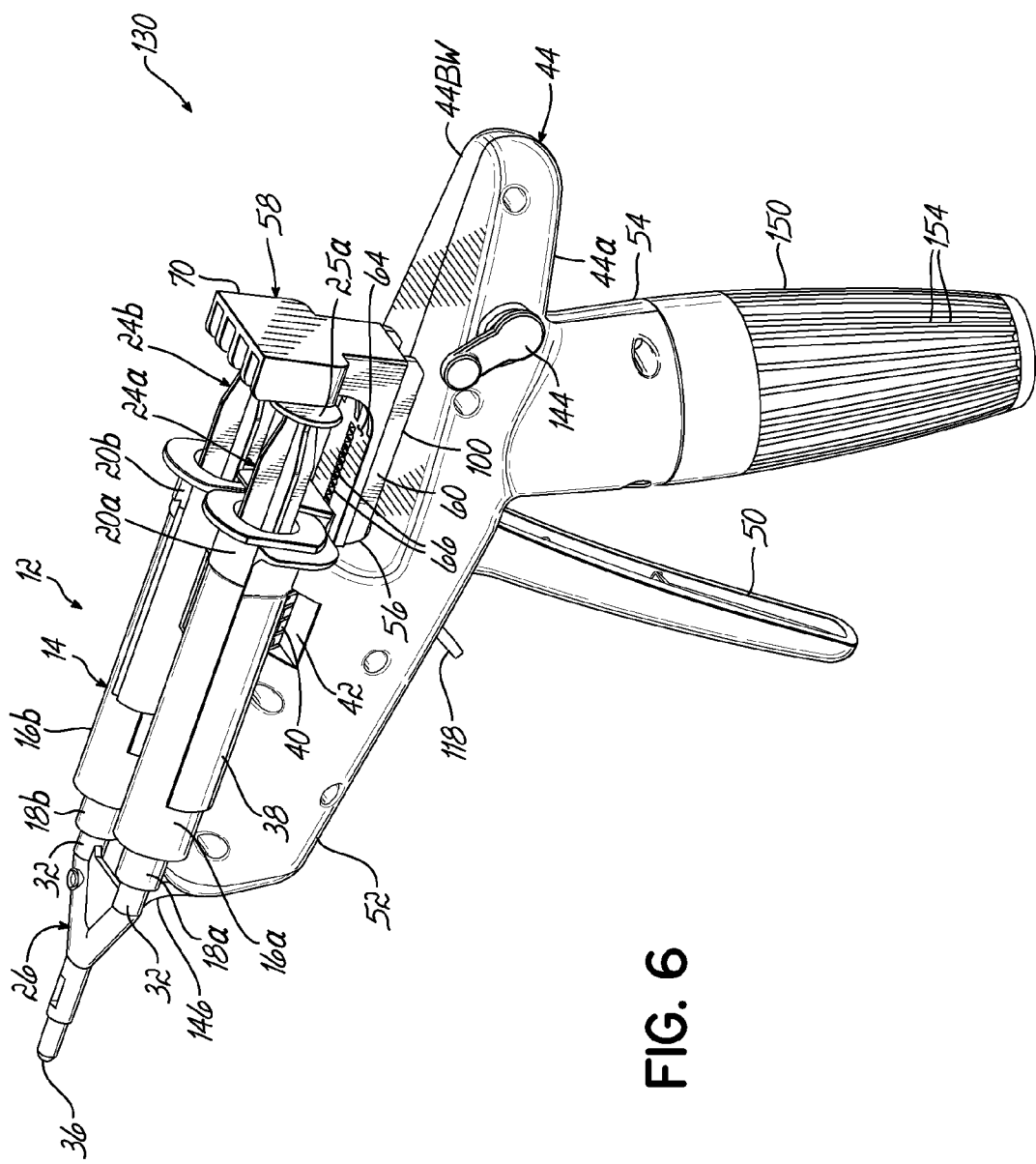
Figure 7:
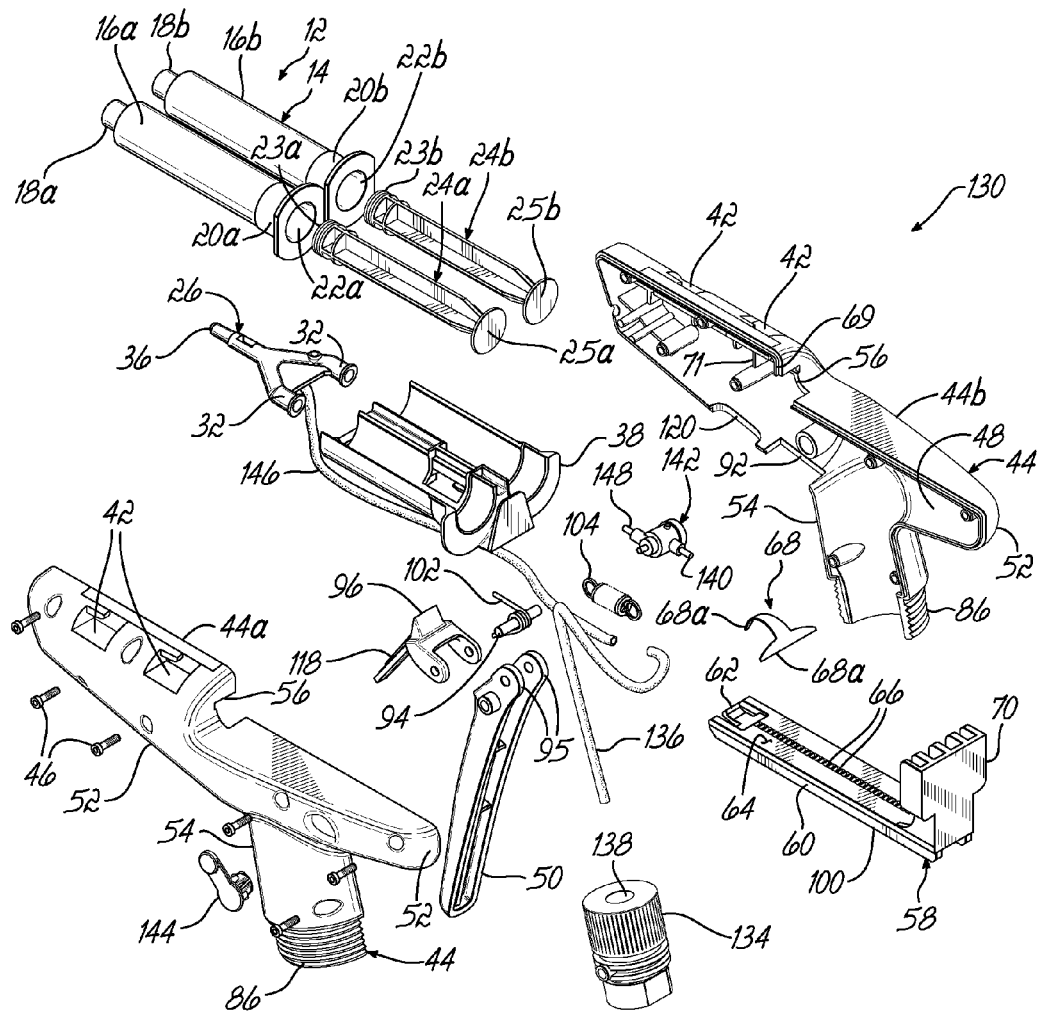
Figure 8:
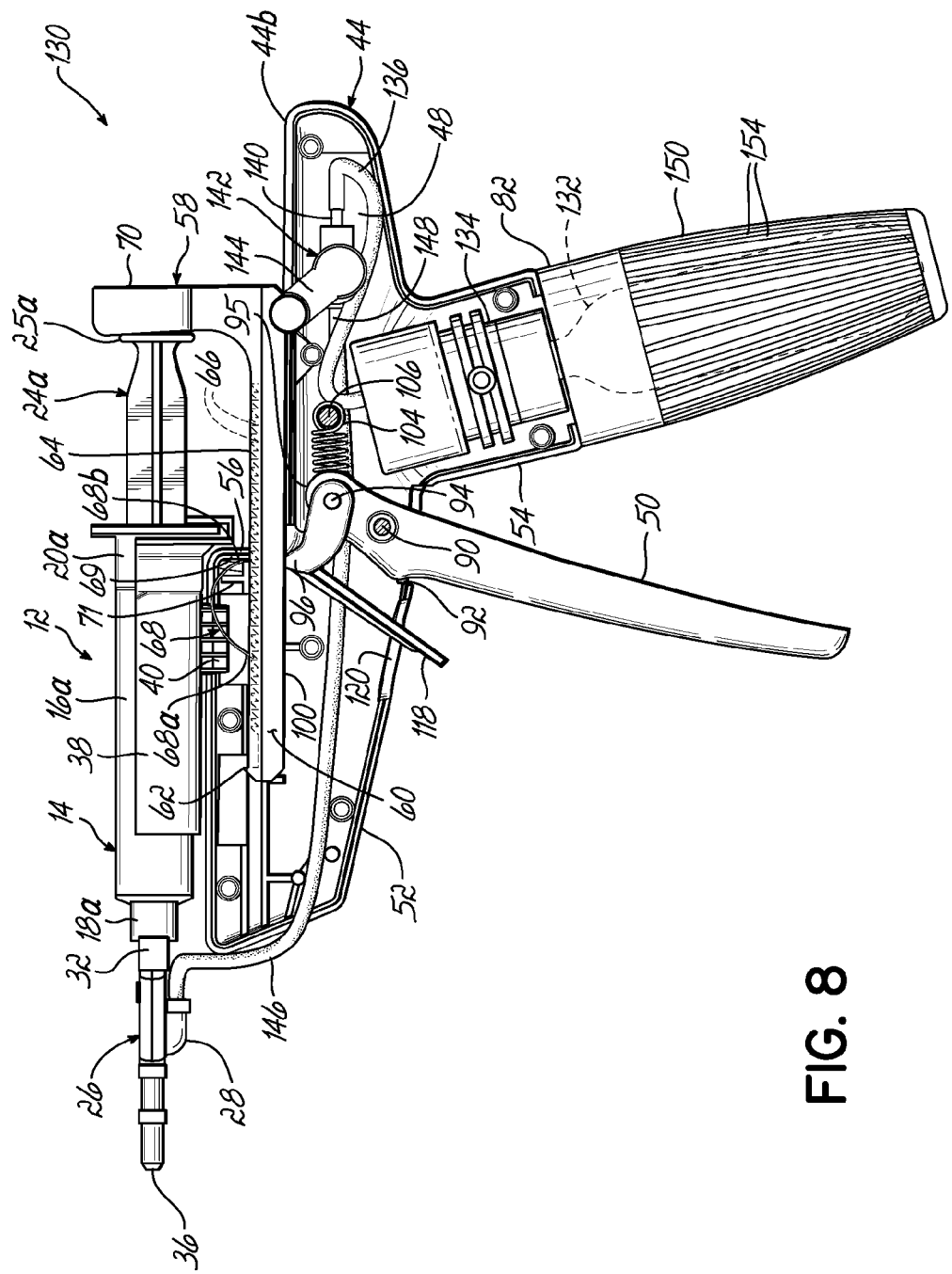

FIG. 8 is side-elevational view of the gas-assisted fluid-dispensing device of FIG. 6 with a left side of the housing removed.

DETAILED DESCRIPTION

Figure 1:
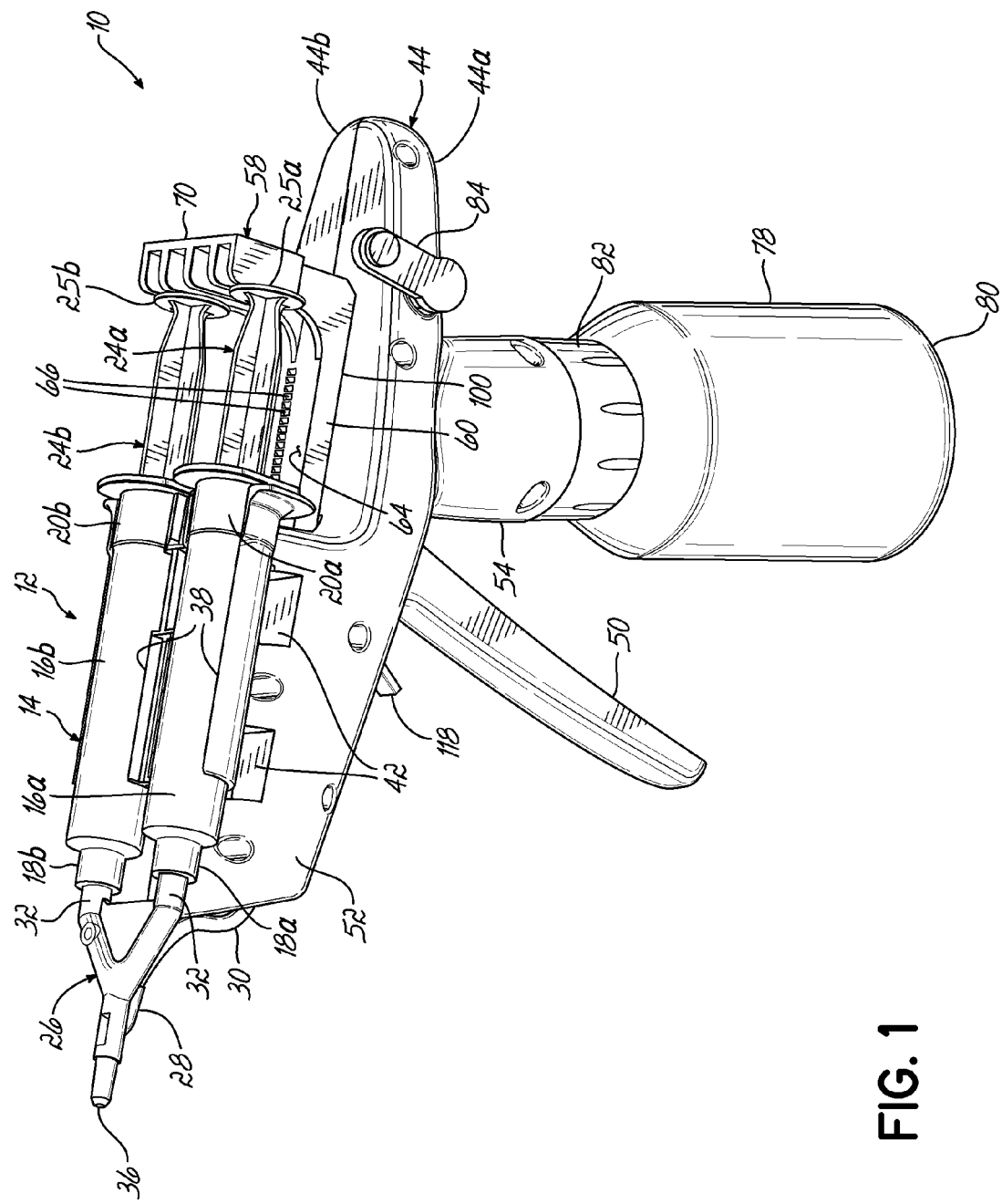
Figure 2:
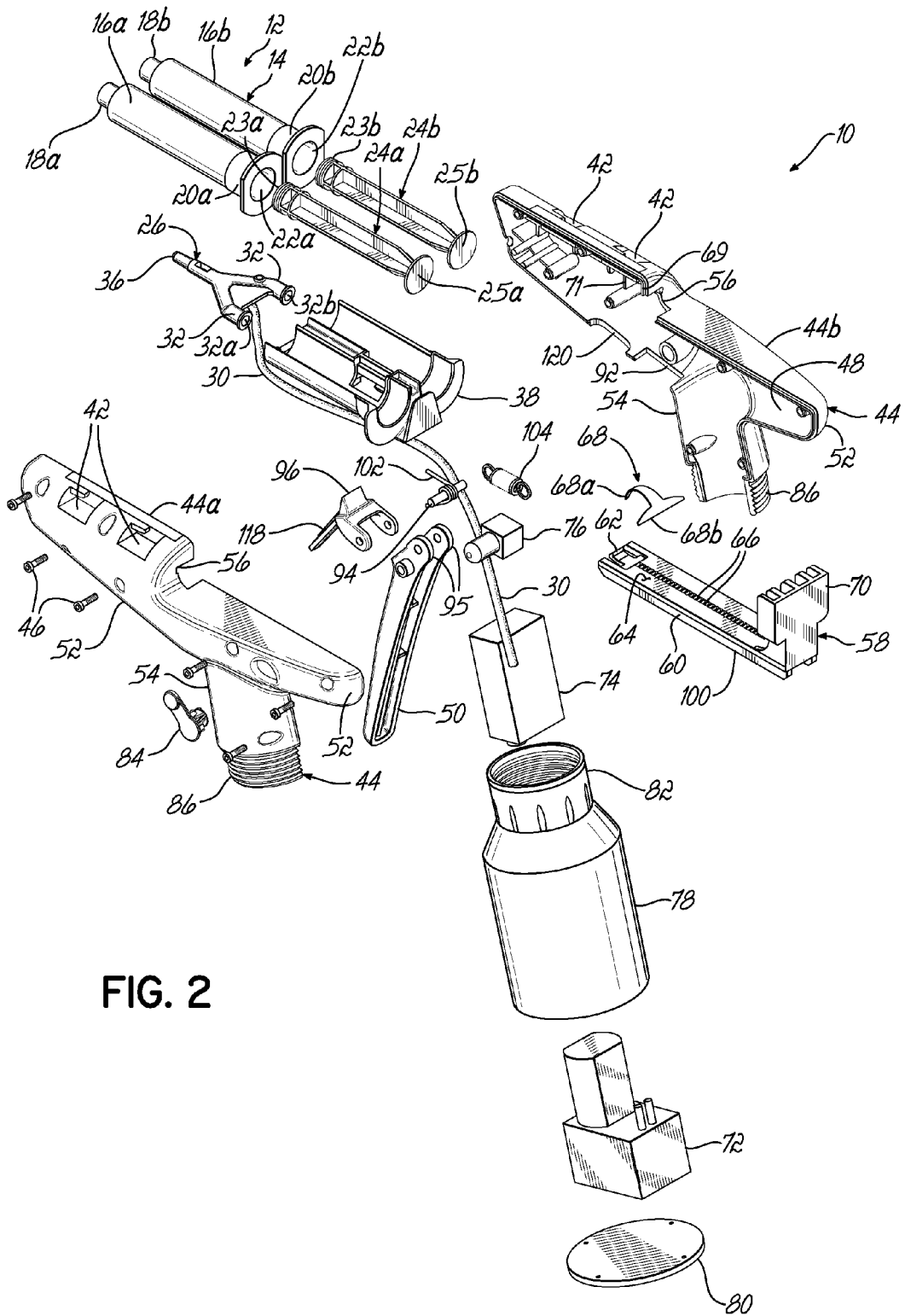

Turning now to the figures, and in particular to FIGS. 1 and 2, where one embodiment of a gas-assisted fluid dispenser ("dispenser" 10) is shown and described in detail. The dispenser 10 includes a fluid-dispensing device 12 having a least one fluid source 14. The fluid source 14 may include, for example, a syringe 14 having one or more parallel fluid chambers (two fluid chambers 16a, 16b are shown) for simultaneously dispensing one or more fluids, such as topical or therapeutic medicinal agents. Moreover, it would be readily appreciated that if more than one fluid is administered, equal volume need not be dispensed. Instead, the volume of a first fluid dispensed from the first fluid chamber 16a may be larger than the volume of a second fluid dispensed from the second fluid chamber 16b. Each of the fluid chambers 16a, 16b includes a tapered distal end 18a, 18b, a proximal end 20a, 20b, and a lumen 22a, 22b extending therebetween. A plunger 24a, 24b resides, at least partially, within the lumen 22a, 22b of each fluid chamber 16a, 16b and extends proximally therefrom. Each plunger 24a, 24b may be constructed in a known, conventional manner and include a distally-positioned stopper 23a, 23b and a proximally-positioned plunger head 25a, 25b.

A spray nozzle tip 26 is coupled to the syringe 14. And, because the syringe 14 of the illustrative embodiment includes two fluid chambers 16a, 16b, the spray nozzle tip 26 is illustrated as a Y-connector attached to both tapered distal ends 18a, 18b of the fluid chambers 16a, 16b. The spray nozzle tip 26 further includes a gas inlet 28 configured to receive a gas line 30. Thus, the spray nozzle 26, as shown, includes two fluid inlets 32a, 32b, one gas inlet 28, and one outlet 36. One of ordinary skill in the art would readily appreciate that the shape of the outlet 26 may be configured to provide a desired aerosol effect. That is, a desired direction and/or spread of the resultant aerosol, along with the gas pressure, may be determined by incorporating a particular design for the outlet 26.

The fluid source 14 is supported within a source holder 38, which may have a molded polymeric material construction that is sized and shaped to accommodate the syringe 14. Accordingly, various sizes, shapes, and configurations of holders 38 are possible for supporting one or more fluid chambers 16a, 16b of similar or varying sizes. The holder 38 includes one or more tabs 40, which are configured to couple the fluid source 14 to a docking port 42 of a housing 44 of the dispenser 10. The docking port 42 may include one or more slots that receive respective ones of the one or more tabs 40.

The housing 44, as shown in FIG. 2, may be constructed as two halves (left half 44a and right half 44b) from a moldable polymeric material, which may be joined by screws 46 to enclose an internal cavity 48. A trigger 50 is coupled to the housing 44 and operably coupled to the fluid-dispensing device 12.

The housing 44 further includes a first, upper housing portion 52 and a second, lower housing portion 54 that is configured as a handle extending angularly downward from the upper housing portion 52.

Figure 3:
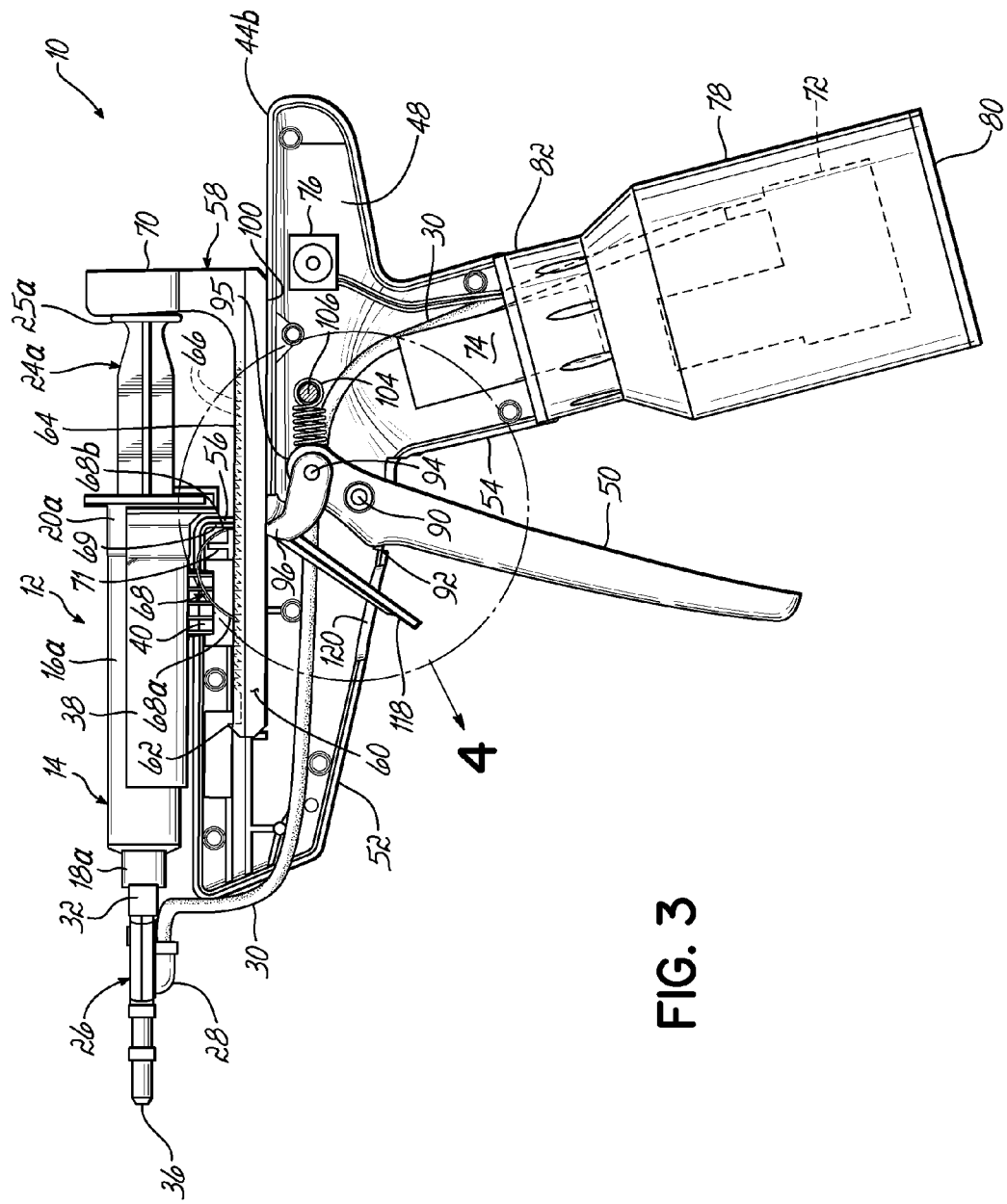

Referring now to FIGS. 1-3, the upper housing portion 52 includes a slot 56 through which an actuating member 58 for the fluid-dispensing device 12 extends. That is, the actuating member 58 is operably coupled to the syringe 14 for dispensing the fluid from the syringe 14 into the spray nozzle tip 26. As shown, the actuating member 58 is a T-shaped slide having an elongated base portion 60 that extends through the slot 56 and configured to slide horizontally relative thereto. A distal end of the base portion 60 may include an end clip 62 extending upwardly therefrom and sized to engage an inner surface of the housing 44 at the slot 56 to prevent inadvertent removal of the slide 58 from the housing 44.

A top surface 64 of the base portion 60 of the slide 58 includes a longitudinal array of indentations 66 extending a substantial portion of the length of the base portion 60. A spring 68, illustrated as generally having a T-shape, is positioned within the cavity 48 between the top surface 64 of the base portion 60 and an inner surface of the upper housing portion 52. A distal end 68a of the spring 68 engages one of the indentations 66 and is configured to maintain the relative position of the slide 58 during operation and reloading of the dispenser 10. An enlarged proximal end 68b secures the spring 68 in its position defined by first and second walls 69, 71 within the cavity 48.

The slide 58 further includes an upright portion 70 that extends substantially orthogonally upward from the base portion 60 and is configured to engage the plunger heads 25a, 25b of the plungers 24a, 24a and actuate the plungers 24a, 26b to dispense the fluid to the spray nozzle tip 26 as subsequently described.

Referring now to FIGS. 2 and 3, the gas line 30 that is coupled to the gas inlet 28 extends through the housing 44 to a self-contained pressurized gas source 72, which is illustrated as an air pump, coupled to the housing 44. The particular embodiment of FIGS. 2 and 3 shows the air pump 72 operably coupled to the lower housing portion 54 such that the air pump 72 moves with the housing 44. The air pump 72 may be any suitable commercially-available air pump that is capable of producing gas pressures ranging from about 15 psi to about 20 psi. While not shown, the air pump 72 may include an internal filter for removing air contaminants and/or microbes from the intake air before dispensing the air to the spray nozzle 26. One exemplary filter may be any 0.2 μm pore-size filter; however, other filters may be used as necessary. The air pump 72 is operably coupled to a power source 74, for example, a battery, by a switch 76. The power source 74 may be positioned within the lower housing portion 54 and the switch 76 positioned on the upper housing portion 52; however, these relative positions should not be considered to be limiting. A lever 84 (FIG. 1) may be coupled to the switch 76 for ease of operation with a gloved hand.

Activating the switch 76 to an "on" position causes the air pump 72 to draw in ambient air from the operating room and to dispense the air to the gas line 30. The dispensed air moves along the gas line 30 and is ejected from the spray nozzle tip 26 at the outlet 36 as a dispersing gas. The dispersing gas in continually ejected from the outlet 36 until the switch 76 is deactivated (i.e., the "off" position).

A surround 78 may be coupled to the lower housing portion 54 to encompass the air pump 72 and/or the power source 74. The particular surround 78 of FIGS. 2 and 3 includes a closed end 80 and a threaded end 82. The closed end 80 may be semi-porous for supplying air for the air intake of the air pump 72. The threaded end 82 is threaded to match a series of threads 86 on the lower housing portion 54. Thus, the surround 78 may be removed by twisting, or unscrewing, the surround 78 from the lower housing portion 54. Alternatively, though not shown, the air pump 72 and/or the power source 74 may be directly coupled to the housing 44 and unsecured by the external surround 78.

With reference specifically now to FIGS. 2 and 3, the details of the actuating member 58 for dispensing the fluid from the syringe 14 into spray nozzle tip 26 to be atomized by the dispersing gas, thereby forming the aerosol, are shown and described. The trigger 50 is operably coupled to the housing 44 at a first pivot point 90 and extends distally therefrom through a trigger slot 92 within the housing 44. The length of the trigger 50 extending from the trigger slot 92 creates a mechanical advantage over direct manipulation of the plungers 24a, 24b. While the length of the trigger 50 may be adjusted to achieve a particular mechanical advantage, one exemplary mechanical advantage may be 4:1.

A proximal end 95 of the trigger 50 is positioned within the cavity 48 of the housing 44 and includes a second pivot point 94 between the trigger 50 and a pawl 96, which includes a connected release arm 118 discussed in detail below. The pawl 96 extends angularly upwardly from the second pivot point 94 and engages a linear array of teeth 98 formed in a bottom surface 100 of the base portion 60 of the slide 58. A biasing spring 102 that is coupled to the trigger 50, biases the pawl 96 upwardly and away from the trigger 50 toward the plurality of teeth 98. A tension spring 104 extends rearwardly from the second pivot point 94 to a fixed point 106 within the cavity 48 of the housing 44 to bias the trigger 50 in a forwardly-directed, unengaged position.

In use, and with reference now to FIGS. 4 and 5, engaging the trigger 50, i.e., directing the trigger 50 toward the lower housing portion 54, causes the proximal end 95 of the trigger 50 to move forward within the cavity 48 (e.g., toward the spray nozzle tip 26). Because the pawl 96 is coupled to the proximal end 95 of the trigger 50 at the second pivot point 94, movement of the trigger 50 will cause the pawl 96 to rotate forward about the second pivot point 94 and apply a forwardly-directed force onto a rear surface 98a of the associated tooth 98. The force will direct the slide 58 forward. With sufficient engagement of the trigger 50 and forward movement of the pawl 96, the slide 58 moves forward a sufficient distance that the pawl 96, when the trigger 50 is released, will engage a proximally-positioned tooth 98. Meanwhile, the distal end 68a of the spring 68 will slide between successive ones of the indentations 66 and maintain the position of the slide 58 relative to the housing 44.

This ratcheting movement of the slide 58 causes the upright portion 70 of the slide 58 to actuate the plungers 24a, 24a. Each engagement (or squeezing) of the trigger 50 is thus converted into a horizontal, distally-directed translation of the upright portion 70 of the slide 58 and thereby directs the plungers 24a, 24b into the lumens 22a, 22b of the fluid chambers 16a, 16b. As the plungers 24a, 24b move inwardly, the fluid is compressed within each of the respective fluid chambers 16a, 16b and a volume of the fluid that is proportional to the linear displacement of the plungers 24a, 24b is dispensed from the tapered distal ends 18a, 18b into the spray nozzle tip 26. Accordingly, metering of the amount of fluid dispensed may be accomplished by the number of trigger compressions, e.g., each complete trigger engagement may cause the pawl 96 to engage every tooth 98 or, alternatively, engage only selected teeth 98. For example, in one embodiment each complete trigger engagement could result in the pawl 96 engaging every second tooth 98 (i.e., a 1:2 ratio of trigger engagements to teeth 98). Accordingly, a partial trigger engagement may be possible to dispense a smaller volume of fluid (for example, a half trigger engagement would engage each tooth 98).

As the fluids are released from the fluid chambers 16a, 16b into the spray nozzle tip 26, the dispensing gas, which is also moving through the spray nozzle tip 26, is mixed with and atomizes, or disperses, the fluids as a treatment aerosol from the outlet 36 of the spray nozzle tip 26. The surgeon may continue dispensing the treatment aerosol by further compressing the trigger 50. Without further compression of the trigger 50, only the dispensing gas is released from the spray nozzle tip 26.

While not shown, it would be possible to include the functional operation of the switch 76 within the trigger 50. Because it is generally desired to ensure that the dispensing gas is fully operational prior to dispensing the fluids from the syringe 14 to ensure a well-generated aerosol, it may be necessary to include a two-position activation of the trigger 50. Accordingly, a first position of the trigger 50 could activate the air pump 72 while a second position of the trigger 50 could actuate the pawl 96. Other arrangements and configurations are possible and would be known to those of ordinary skill in the art.

After some use, it may be necessary to reload the dispenser 10 with another syringe 14 for use with the same patient or in preparation for another surgery. Accordingly, the fluid-dispensing device 12 may need to be removed and replaced with another fluid-dispensing device 12. Because the pawl 96 is designed as a one-way ratchet, reverse movement of the slide 58 is not possible without first releasing the pawl 96 from the plurality of teeth 98. The release arm 118, which is coupled with the pawl 96, extends through an arm slot 120 of the housing 44 and is externally accessible to the surgeon. Biasing the release arm 118 rearwardly (i.e., toward the trigger 50) rotates the pawl 96 against the bias of the biasing spring 102 and rotates the pawl 96 about the second pivot point 94 to withdraw the pawl 96 from the plurality of teeth 98. Accordingly, the slide 58 may be retracted rearwardly and the syringes 14 removed. While the spring 68 is configured to maintain the relative position of the slide 58, manual manipulation of the slide 58 is sufficient to overcome the resistance created between the distal end 68a of spring 68 and the indentations 66.

Turning now to FIGS. 6-8, a gas assist fluid-dispensing device ("dispenser" 130) in accordance with another embodiment of the invention is shown and described in detail and where like numbers reference like features described previously. In this particular illustrative embodiment, a self-contained pressurized gas source 132 is coupled to the housing 44 and is specifically illustrated as a cylinder of compressed air. Even more particularly, the cylinder 132 is coupled to the housing 44 through a tank regulator 134. The cylinder 132 of compressed air and the regulator 134 may be any suitable commercially-available tank and regulator known to those of ordinary skill in the art and capable of producing air pressures ranging from about 15 psi to about 20 psi. The regulator 134 may be secured within the cavity 48 of the lower housing portion 54. The cylinder 132, which is sealed to prevent premature release of compressed air from the cylinder 132, may be coupled to the regulator 134, at the time of surgery, in a way that breaches the seal and allows compressed air to enter the regulator 134.

While the dispenser 130 may be constructed as a disposable instrument for one use only, the regulator 134 may be configured to release a used, or partially used, cylinder 132 such that a new cylinder 132 may later be coupled to the regulator 134. Accordingly, the housing 44, along with the regulator 134 that is coupled to the housing 44, may be constructed in a manner that allows the dispenser 130 to be sterilized before subsequent uses. Such sterilization methods may include autoclaves or others that are generally known.

Compressed air that enters the regulator 134 enters a first gas line 136 coupled to an aperture 138 (FIG. 7) of the regulator 134 that extends to an inflow port 140 of a valve 142 operable by a lever 144. A second gas line 146 extends between an outflow port 148 of the valve 142 to the gas inlet 28 of the spray nozzle tip 26. Moving the lever 144 opens the valve 142 and allows compressed air to enter the second gas line 146 and exit the spray nozzle tip 26 as dispensing air. The flow of dispensing air continues until the valve 142 is closed by reversing the movement of the lever 144.

Because the release of pressurized air from the cylinder 132 creates a substantial drop in the temperature of the cylinder 132, a cover 150 may be included to surround the cylinder 132 for insulating the cylinder 132 and improving the surgeon's comfort. The cover 150 may include a threaded portion 152 that cooperates with the threads 86 of the lower housing portion 54 and, if desired, ribbing 154 that further spaces the surgeon's hand away from the cylinder 132.

Use of the dispenser 130 is similar to the dispenser 10 of FIG. 1. Briefly, the surgeon activates the release of compressed air from the cylinder 132 by moving the lever 144 associated with the valve 142. Compressed air is then dispensed from the outlet 36 of the spray nozzle tip 26. The surgeon may then engage the trigger 50 such that the ratcheting action of the pawl 96 advances the slide 58 and dispenses fluids into the spray nozzle tip 26. The fluid within the spray nozzle tip 26 is atomized by the dispensing air and released as an aerosol from the outlet 36 of the spray nozzle tip 26. Further engagements of the trigger 50 continues to release the aerosol from the spray nozzle tip 26. Ceasing the engagement discontinues the release of the aerosol and only dispensed air exits the spray nozzle tip 26. Further dispensing of air may be terminated by closing the valve 142.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A gas-assisted fluid-dispensing device configured to deliver an aerosol onto a surgical site, the fluid-dispensing device comprising:
   a syringe configured to contain a fluid, the syringe including a distal end and a proximal end with a plunger extending from the proximal end;
   a spray nozzle tip coupled to the distal end of the syringe and configured to generate the aerosol;
   a housing including a first housing portion, a second housing portion configured as a handle, and a docking port on the first housing portion configured to receive the syringe;
   a trigger coupled to the housing;
   an actuating member coupled to the first housing portion and operatively coupled to the trigger, the actuating member configured to apply a force to the plunger of the syringe to discharge the fluid from the syringe into the spray nozzle tip when the trigger is actuated;
   a self-contained pressurized gas source coupled to the housing for movement with the housing, and the pressurized gas source further operatively coupled to the spray nozzle tip; and
   a control mechanism operable to control delivery of a pressurized gas from the pressurized gas source to the spray nozzle tip for atomizing the fluid within the spray nozzle tip and generating the aerosol, the control mechanism operable to control delivery of the pressurized gas independent of the operation of the trigger.

2. The gas-assisted fluid-dispensing device of claim 1, wherein the pressurized gas source is a battery-powered air pump, and the control mechanism is a power switch operatively coupled to the air pump.

3. The gas-assisted fluid-dispensing device of claim 1, wherein the pressurized gas source is a compressed gas cylinder, and the control mechanism includes a regulator coupled to the pressurized gas source and a valve configured to control a flow of the pressurized gas from the regulator to the spray nozzle tip.

4. The gas-assisted fluid-dispensing device of claim 1, wherein the actuating member includes an actuating slide configured to slide along the first housing portion and to apply the force to the plunger of the syringe.

5. The gas-assisted fluid-dispensing device of claim 1, wherein the pressurized gas source is disposed within the second housing portion.

6. The gas-assisted fluid-dispensing device of claim 1, wherein the trigger is operable to control delivery of the fluid independent of the operation of the gas such that the trigger and control unit allow selection and operation of dispensing only gas, dispensing only fluid, and simultaneously dispensing pressurized gas and fluid.

7. An actuator gun configured for use with a gas-assisted fluid-dispensing device configured to deliver an aerosol onto a surgical site, the gas-assisted fluid-dispensing device including a syringe containing a fluid and a spray nozzle tip, the actuator gun comprising:
   a housing including a first housing portion, a second housing portion configured as a handle, and a docking port on the first housing portion configured to receive the gas-assisted fluid-dispensing device;
   a trigger coupled to the housing;
   an actuating member coupled to the first housing portion and operatively coupled to the trigger, the actuating member configured to apply a force to the syringe to discharge the fluid from the syringe into the spray nozzle tip when the trigger is actuated;
   a self-contained pressurized gas source coupled to the housing for movement with the housing, and the pressurized gas source further operatively coupled to the spray nozzle tip; and
   a control mechanism operable to control delivery of a pressurized gas from the pressurized gas source to the spray nozzle tip for atomizing the fluid within the spray nozzle tip and generating the aerosol, the control mechanism operable to control delivery of the pressurized gas independent of the operation of the trigger.

8. The actuator gun of claim 7, wherein the pressurized gas source is a battery-powered air pump, and the control mechanism is a power switch operatively coupled to the air pump.

9. The actuator gun of claim 7, wherein the pressurized gas source is a compressed gas cylinder, and the control mechanism includes a regulator coupled to the pressurized gas source and a valve configured to control a flow of the pressurized gas from the regulator to the spray nozzle tip.

10. The actuator gun of claim 7, wherein the actuating member includes an actuating slide configured to slide along the first housing portion and to apply a force to the syringe.

11. The actuator gun of claim 7, wherein the pressurized gas source is disposed within the second housing portion.

12. The actuator gun of claim 7, wherein the control mechanism and the trigger independently control a flow of the pressurized gas from the pressurized gas source and a flow of the fluid from the syringe into the spray nozzle tip.

13. A method of dispensing an aerosol onto a surgical site with a fluid-dispensing device including a syringe containing a fluid, a spray nozzle tip coupled to the syringe, a housing including a first housing portion coupled to the syringe and a second housing portion configured as a handle, a trigger coupled to the housing, and a self-contained pressurized gas source coupled to the housing for movement with the housing, the method comprising:
- actuating the pressurized gas source to supply a pressurized gas to the spray nozzle tip;
- engaging the trigger to deliver fluid from the syringe to the pressurized gas in the spray nozzle tip independent of actuating the pressurized gas source;
- atomizing the fluid within the spray nozzle tip with the pressurized gas to form the aerosol; and
- dispensing the aerosol from the spray nozzle tip onto the surgical site.

14. The method of claim 13, wherein the pressurized gas source is a battery-powered air pump including a power switch, and actuating the pressurized gas source further comprises:
- actuating the power switch to start the battery-powered air pump and to enable a flow of a pressurized air from the air pump to the spray nozzle tip.

15. The method of claim 13, wherein the pressurized gas source is a compressed gas cylinder, the fluid-dispensing device further includes a valve operatively coupled to the compressed gas cylinder, and actuating the pressurized gas source further comprises:
- opening the valve to enable a flow of the pressurized gas from the compressed gas cylinder to the spray nozzle tip.

16. The method of claim 13, further comprising:
- independently controlling the actuation of the pressurized gas source and the engaging of the trigger to modify an amount of the fluid atomized by the pressurized gas in the spray nozzle tip.

17. A gas-assisted fluid-dispensing device configured to deliver an aerosol onto a surgical site, the fluid-dispensing device comprising:
- a syringe configured to contain a fluid, the syringe including a distal end and a proximal end with a plunger extending from the proximal end;
- a spray nozzle tip in fluid communication with the distal end of the syringe and configured to generate the aerosol;
- a housing including a docking port configured to receive the syringe;
- a trigger operatively coupled to the plunger;
- an actuating member operatively coupled to the trigger, the actuating member configured to apply a force to the plunger of the syringe to discharge the fluid from the syringe into the spray nozzle tip when the trigger is actuated;
- a self-contained pressurized gas source in fluid communication with the spray nozzle tip; and
- a control mechanism operable to control delivery of a pressurized gas from the pressurized gas source to the spray nozzle tip for atomizing the fluid within the spray nozzle tip and generating the aerosol, the control mechanism operable to control delivery of the pressurized gas independent of the operation of the trigger.

* * * * *